United States Patent [19]

Chiodoni et al.

[11] 4,378,359
[45] Mar. 29, 1983

[54] THEOPHYLLINYLMETHYLDIOXOLANE DERIVATIVES, METHODS FOR THEIR PREPARATION AND PHARMACEUTICAL COMPOSITIONS CONTAINING THEM

[75] Inventors: Ugo Chiodoni, Milan; José S. Franzone, Turin; Silvano Spinelli, Trecate, all of Italy

[73] Assignees: Istituto Biologico Chemioterapico "ABC" S.p.A., Turin; Unibios S.p.A, Novara, both of Italy

[21] Appl. No.: 251,485

[22] Filed: Apr. 6, 1981

[30] Foreign Application Priority Data

Apr. 15, 1980 [IT] Italy .................. 21370 A/80

[51] Int. Cl.³ .................. A61K 27/00; A61K 31/52; C07D 473/00
[52] U.S. Cl. .................. 424/248.57; 424/253; 544/118; 544/267; 544/271
[58] Field of Search .................. 544/118, 267, 271; 424/248.57, 253

[56] References Cited

U.S. PATENT DOCUMENTS 2,761,861  9/1956  Doebel et al. .................. 544/267
2,840,559  6/1958  Krantz, Jr. et al. .................. 544/267
3,734,911  5/1973  Bestian .................. 544/271

FOREIGN PATENT DOCUMENTS 1523273  3/1968  France .................. 544/267

OTHER PUBLICATIONS

Chem. Abstracts 61: 662b.

Primary Examiner—Ethel G. Love
Attorney, Agent, or Firm—Bucknam and Archer

[57] ABSTRACT

Compounds of the following general formula

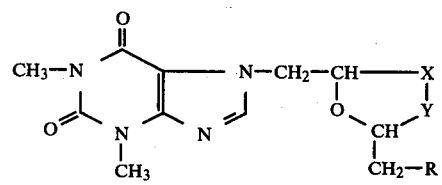

wherein: X and Y are different from each other and represent —$CH_2$— or an oxygen atom; R represents a radical selected from hydroxy, bromo, acetoxy, pyrrolidino, morpholino, piperazino and piperazino substituted at the position 4 by a carbethoxy, benzyl, phenyl, halophenyl, methoxyphenyl or trifluoromethylphenyl group, or when X is —$CH_2$— and Y is an oxygen atom, R may represent also chloro; methods for their preparation; pharmaceutical compositions containing them. The compounds possess a remarkable antitussive activity.

12 Claims, No Drawings

THEOPHYLLINYLMETHYLDIOXOLANE DERIVATIVES, METHODS FOR THEIR PREPARATION AND PHARMACEUTICAL COMPOSITIONS CONTAINING THEM

DESCRIPTION OF THE INVENTION

The present invention relates to new theophyllinylmethyldioxolone derivatives of the following general formula

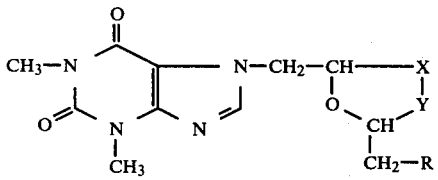

wherein:

X and Y are different from each other and represent —$CH_2$— or an oxygen atom; R represents a radical selected from hydroxy, bromo, acetoxy, pyrrolidino, morpholino, piperazino and piperazino substituted at the position 4 by a carbethoxy, benzyl, phenyl, halophenyl, methoxyphenyl or trifluoromethyl group; or when X is —$CH_2$— and Y is an oxygen atom, R may also represent chloro.

A preferred group of compounds comprises those compounds of formula I wherein X and Y are different from each other and represent —$CH_2$— or an oxygen atom, R represents a radical selected from bromo, acetoxy, pyrrolidino, morpholino and piperazino and, when X is —$CH_2$— and Y is an oxygen atom, R may also represent chloro.

A further object of the invention is represented by the methods for the preparation of the compounds of formula I.

A third object of the invention is represented by the pharmaceutical compositions useful for combatting cough diseases which contain as the active ingredient or ingredients one or more of the compounds of the above formula I.

According to an aspect of the present invention, the compounds of formula I wherein X represents an oxygen atom and Y is —$CH_2$— are prepared by contacting a compound of formula

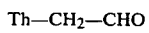  Th—$CH_2$—CHO    II wherein Th is the radical 7-theophyllinyl-, with a compound of the general formula

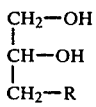

wherein R has the meanings illustrated above, according to the following reaction scheme

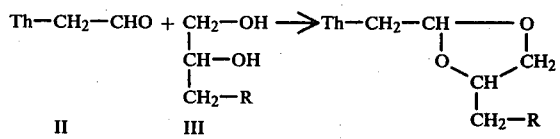

The reaction is carried out at a temperature comprised between about 60° and about 150° C., in a solvent system which is preferably represented by an aromatic hydrocarbon such as, for instance, benzene, toluene or xylene, or a mixture thereof, and in the presence of an acidic catalyst. The reaction temperature is advantageously adjusted at the reflux temperature of the mixture and the water which forms during the reaction course is azeotropically distilled off. Alternatively, the compounds of formula I wherein X is again an oxygen atom and Y is —$CH_2$— may be obtained from the 2-(7'-theophyllinylmethyl)-4-chloromethyldioxolane (prepared as described by De Martiis, Rend. Ist. Super. Sanita, 26 (10-11) 770, 1963) or the corresponding bromo-derivative by means of a nucleophilic substitution reaction. Thus, it is possible to prepare the compounds of formula I wherein R is different from halogen i.e. the pyrrolidino-, morpholino-, and piperazinomethyldioxolanes, wherein the piperazino ring may be substituited at the position 4 by a carbethoxy, benzyl, phenyl, halophenyl, methoxyphenyl or trifluoromethylphenyl group, or the acetoxymethyl-dioxolanes, by reacting the 2(7'-theophyllinylmethyl)-4-chloromethyl- or -4-bromomethyl-dioxolane with the corresponding bases, or a metal acetate in the absence of any solvent or in a solvent such as, for instance, dimethylformamide or hexamethylphosphoramide. These solvents are particularly suitable for obtaining the corresponding acetoxymethyl derivative (compound of formula I in which X=oxygen, Y=—$CH_2$— and R=$CH_3COO$—) starting from the above cited halomethyldioxolanes. These nucleophilic substitution reactions are in some instances favored by the employment of metal catalysts such as, for instance, copper, or phase transfer catalyst such as, for instance, Aliquat 336$^R$.

According to another aspect of the invention, the compounds of formula I wherein X is —$CH_2$— and Y is an oxygen atom may be prepared by reacting the 7-(2,3-bis-hydroxypropyl)-theophyllin of formula

  Th—$CH_2$—CHOH—$CH_2OH$    IV wherein Th is the radical 7-theophyllinyl- with a predetermined acetaldehyde derivative of formula

wherein R is defined as above, according to the following reaction scheme

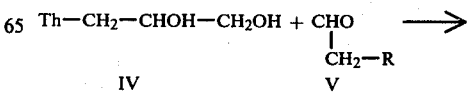

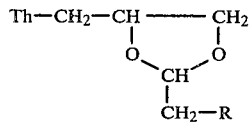

Instead of the acetaldehyde derivatives of formula V, the corresponding acetals may even be advantageously employed. Also in this case, it may be first achieved the dioxolanes of formula I wherein X is —CH$_2$—, Y is an oxygen atom and R may be bromo or chloro, which may in turn be transformed into the corresponding dioxolanes wherein R is different from bromo and chloro by means of the above illustrated nucleophilic substitution reaction.

The following examples are given with the purpose of better illustrating some preferred embodiments of the invention but in no way they must be construed as a limitation of the invention itself.

Example 1—2-Bromomethyl-4-(7′-theophyllinylmethyl)-dioxolane (Compound of formula I wherein X=—CH$_2$—, Y=O and R=Br). A mixture of 20 g (0.078 mole) of 7-(2,3-bis-hydroxypropyl)theophyllin, 24.26 ml (0.157 mole) of bromoacetaldehyde diethylacetal and 0.4 g of anhydrous sulphosalicyclic acid was heated at 140° C. for 5 hours. During this time, about 15 ml of ethanol were distilled off. The gelatinous mass which formed upon cooling was washed by decantation with 50 ml of an aqueous 20% solution of potassium bicarbonate. The obtained residue was extracted three times with 50 ml of chloroform, total chloroform=150 ml), the chloroform extracts were collected, dried over sodium sulphate and evaporated to dryness. A product was obtained, which was crystallized from isopropanol. Yield: 24.9 g of a crystalline product, showing a unitary thin layer chromatography (TLC) pattern. M.p. 136° C.

| Elemental Analysis for C$_{12}$H$_{15}$BrN$_4$O$_4$ (MW = 359) | | | |
|---|---|---|---|
| | % C | % H | % N |
| Calc. | 40.11 | 4.18 | 15.60 |
| Found | 40.22 | 4.09 | 15.44 |

Example 2—4-Pyrrolidinomethyl-2-(7′-theophyllinyl)-dioxolane (Compound of formula I wherein X=O, Y=CH$_2$, R=pyrrolidino)

A solution of 5 g (0.0159 mole) of 2-(7′-theophyllinylmethyl)-4-chloromethyl-dioxolane and 2.84 ml (0.032 mole) of pyrrolidine in 30 ml of benzene was heated for 20 hours at 125° C., under pressure. Upon cooling, the reaction mixture was vigorously shaken with 20 ml of water containing 1.92 g (0.032 mole) of acetic acid. The aqueous solution was decolored with activated coal, made alcaline by means of sodium hydroxide and extracted three times with 10 ml of benzene (total benzene=30 ml). The benzene extracts were collected, dried over potassium carbonate and concentrated in vacuo. The obtained residue was crystellized from isopropanol. Yield: 3.4 g of colorless crystalline product. M.p. 80° C.

| Elemental analysis for C$_{16}$H$_{23}$N$_5$O$_4$ (MW = 349) | | | |
|---|---|---|---|
| | % C | % H | % N |
| Calc. | 55.01 | 6.59 | 20.11 |
| Found | 54.85 | 6.57 | 19.84 |

The following compounds were prepared substantially according to the procedure described in Example 2.

(2a)—4-Morpholinomethyl-2-(7′-theophyllinylmethyl)-dioxolane (Compound of formula I wherein X=O, Y=—CH$_2$— and R=morpholino). M.p. 104°–6° C. (from isopropanol).

| Elemental Analysis for C$_{16}$H$_{23}$N$_5$O$_5$ (MW = 365) | | | |
|---|---|---|---|
| | % C | % H | % N |
| Calc. | 52.60 | 6.30 | 19.17 |
| Found | 52.90 | 6.41 | 18.98 |

(2b)—2-Morpholinomethyl-4-(7′-theophyllinylmethyl)-dioxolane (Compound of formula I wherein X=—CH$_2$—, Y=O and R=morpholino).
M.p. 149°–50° C. (from isopropanol)

| Elemental Analysis for C$_{16}$H$_{23}$N$_5$O$_5$ (MW = 365) | | | |
|---|---|---|---|
| | % C | % H | % N |
| Calc. | 52.60 | 6.30 | 19.17 |
| Found | 53.00 | 6.48 | 19.20 |

(2c)—2-(4′-Carbethoxy-piperazinomethyl)-4-(7′-theophyllinylmethyl)-dioxolane (Compound of formula I wherein X=—CH$_2$—, Y=O and R=4-carbethoxy-piperazino). M.p. 162°–63° C. (from isopropanol).

| Elemental Analysis for C$_{19}$H$_{28}$N$_6$O$_6$ (MW = 346) | | | |
|---|---|---|---|
| | % C | % H | % N |
| Calc. | 52.29 | 6.42 | 19.26 |
| Found | 52.45 | 6.58 | 18.98 |

Example 3—4-(4′-Benzyl-piperazinomethyl)-2-(7′-theophyllinylmethyl)-dioxolane (Compound of formula I wherein X=O, Y=—CH$_2$— and R=4-benzyl-piperazino).

A mixture of 5 g (0.0159 mole) of 4-chloromethyl-2-(7′-theophyllinylmethyl)-dioxolane and 5.6 ml (0.0319 mole) of N-benzylpiperazine in 10 ml of hexamethylphosphoramide was heated at 140° C. for 4 hours in the presence of traces of copper. After cooling, the mixture was added with 100 ml of chloroform, the copper was filtered off and the filtrate was washed 5 times with 30 ml. of water (total water=150 ml). After drying the organic phase over sodium sulphate and evaporating off the solvent, a residue was obtained, which was crystallized from isopropanol. Yield: 3.5 g. M.p. 103°–5° C.

| Elemental Analysis for $C_{23}H_{30}N_6O_4$ (MW = 454) | | | |
|---|---|---|---|
| | % C | % H | % N |
| Calc. | 60.8 | 6.65 | 18.50 |
| Found | 61.1 | 6.60 | 18.43 |

The following compounds were prepared substantially according to the procedure described in Example 3.

(3a)-2-(4'-Benzyl-piperazinomethyl)-4-(7'-theophyllinylmethyl)-dioxolane (Compound of formula I wherein X=—CH$_2$—, Y=O and R=4-benzyl-piperazino) M.p. 172°–74° C. (from isopropanol)

| Elemental Analysis for $C_{23}H_{30}N_6O_4$ (MW = 454) | | | |
|---|---|---|---|
| | % C | % H | % N |
| Calc. | 60.8 | 6.65 | 18.50 |
| Found | 60.88 | 6.71 | 18.38 |

(3b)-2-[4'-(p-chlorophenyl)-piperazinomethyl]-4-(7'-theophyllinylmethyl)-dioxolane (Compound of formula I wherein X=—CH$_2$—, Y=O and R=4-(p-chlorophenyl-piperazino) M.p. 176°–78° C. (from isopropanol)

| Elemental Analysis for $C_{22}H_{27}ClN_6O_4$ (MW = 474.5) | | | |
|---|---|---|---|
| | % C | % H | % N |
| Calc. | 55.63 | 5.69 | 17.70 |
| Found | 55.51 | 5.53 | 17.56 |

(3c)-4-[4'-(p-Chlorophenyl)-piperazinomethyl]-2-(7'-theophyllinylmethyl)-dioxolane (Compound of formula I wherein X=O, Y=—CH$_2$— and R=4-(p-chlorophenyl)-piperazino). M.p. 137°–40° C. (from isopropanol)

| Elemental Analysis for $C_{22}H_{27}ClN_6O_4$ (MW = 474.5) | | | |
|---|---|---|---|
| | % C | % H | % N |
| Calc. | 55.63 | 5.69 | 17.70 |
| Found | 55.48 | 5.83 | 17.49 |

Example 4—2-Acetoxymethyl-4-(7'-theophyllinylmethyl)-dioxolane (Compound of formula I wherein X=—CH$_2$—, Y=O and R=acetoxy).

A solution of 5 g (0.013 mole) of 2-bromomethyl-4-(7'-theophyllinylmethyl)-dioxolane and 13.5 g (0.13 mole) of potassium acetate in 20 ml of hexamethylphosphoramide added with 0.12 g of Aliquat 336$^R$ was heated at 140° C. under stirring. After 5 hours the reaction mixture was cooled, added with 100 ml of CHCl$_3$, washed several times with water and finally dried over sodium sulphate. After evaporating the solvent, the residue was washed with little diethylether and crystallized from isopropanol. Yield: 3 g. M.p. 127° C.

| Elemental Analysis for $C_{14}H_{18}N_4O_6$ (MW = 338) | | | |
|---|---|---|---|
| | % C | % H | % N |
| Calc. | 49.70 | 5.32 | 16.56 |
| Found | 49.86 | 5.18 | 16.31 |

Example 5—2-Hydroxymethyl-4-(7'-theophyllinylmethyl)-dioxolane (Compound of formula I wherein X=—CH$_2$—, Y=O and R=hydroxy).

A mixture of 3 g (0.008 mole) of 2-acetoxymethyl-4-(7'-theophyllinylmethyl)-dioxolane, 30 ml of aqueous 20% NaOH and 90 ml of H$_2$O was stirred for two hours at room temperature. The mixture was extracted four times with 20 ml of chloroform (total chloroform=80 ml), the organic phases were collected and dried over sodium sulphate, then the solvent was evaporated off. The obtained residue was taken up with 10 ml of hot isopropanol. Upon cooling, 1.5 g of the title compound crystallized out. M.p. 135°–37° C.

| Elemental Analysis for $C_{12}H_{16}N_4O_5$ (MW = 296) | | | |
|---|---|---|---|
| | % C | % H | % N |
| Calc. | 48.64 | 5.40 | 18.91 |
| Found | 48.72 | 5.31 | 18.68 |

As stated above, the compounds of the invention possess a remarkable antitussive utility coupled with a very low toxicity. In the following, we want to report the favourable biological properties of some representative members of the compounds of formula I.

(A) Acute Toxicity

The experiments for determining the acute toxicity were carried out on male mice (Charles-River Italy breeding) of average body weight of 20-22 g.

The compounds of the invention were administered either by oral route with the aid of a gastric gavage, or by intraperitoneal route through an insuline syringe. The solutions of each compound to be tested were suspended in 0.5% carboxymethylcellulose: each compound was administered at a concentration of 0.1 ml/10 g of body weight.

The results obtained with dosages of 500 mg/kg of body weight are reported in Table 1, whereas the results observed at 1000 mg/kg of body weight are reported in Table 2. Aminophyllin was used in both cases as the comparison substance.

TABLE 1

| Compound of Example | Dosage: 500 mg/kg per os | | | Dosage: 500 mg/kg intraperitoneally | | |
|---|---|---|---|---|---|---|
| | No. of animals | dead/ treated | % mortality | No. of animals | dead/ treated | % mortality |
| 1 | 10 | 0/10 | 0 | 10 | 3/10 | 30 |
| 2 | 10 | 0/10 | 0 | 10 | 0/10 | 0 |
| 2a | 10 | 0/10 | 0 | 10 | 0/10 | 0 |
| 2b | 10 | 0/10 | 0 | 10 | 0/10 | 0 |
| 4 | 10 | 0/10 | 0 | 10 | 0/10 | 0 |
| Aminophyllin | 10 | 5/10 | 50 | 10 | 8/10 | 80 |

TABLE 2

| Compound of Example | Dosage: 1000 mg/kg per os | | | Dosage: 1000 mg/kg intraperitoneally | | |
| --- | --- | --- | --- | --- | --- | --- |
| | No. of animals | dead/treated | % mortality | No. of animals | dead/treated | % mortality |
| 1 | 10 | 8/10 | 80 | 10 | 6/10 | 60 |
| 2 | 10 | 0/10 | 0 | 10 | 6/10 | 60 |
| 2a | 10 | 0/10 | 0 | 10 | 5/10 | 50 |
| 2b | 10 | 0/10 | 0 | 10 | 6/10 | 60 |
| 4 | 10 | 0/10 | 0 | 10 | 0/10 | 0 |
| Aminophyllin | 10 | 10/10 | 100 | 10 | 10/10 | 100 |

(B) antibronchospastic and Antitussive Activities

These biological properties were evaluated on guinea pigs substantially according to the technique of Charlier et al., Arch. Inter. Pharmacodyn. 134, 306, 1961. Said technique essentially consists in exposing the laboratory animal to a 7.5% citric acid aerosol for five minutes and monitoring the cough of the animal before and after the oral treatment with the compounds to be tested. The apparatus for causing and monitoring the cough is constituted by a hermetically sealed plexiglas box (20 by 20 by 15 cm.) which, on one side, is connected via a cannula with the aerosol diffuser and, on the top side, with another cannula which in turn is connected with the transducer of a polygraph.

Male dappled guinea pigs weighing 350-400 g, fasted from 12 hours, were used in the experiments. The obtained results are collected in the following Table 3. As the comparison substance, aminophyllin was again employed.

TABLE 3

| Compound of Example | Dose mg/kg per os | Mean number of cough stroke ± SE | | % Variation over the pre-treatment stage | % Variation over the controls |
| --- | --- | --- | --- | --- | --- |
| | | Before treatment | 3 hours after treatment | | |
| Controls | — | 32.00 ± 3.92 | 30.30 ± 2.40 | −5.4 | — |
| 1 | 10 | 31.50 ± 2.96 | 13.25 ± 4.28 | −57.94 | −56.27 |
| 2 | 10 | 30.50 ± 6.50 | 12.00 ± 1.20 | −60.66 | −60.39 |
| 2a | 10 | 32.00 ± 5.52 | 12.00 ± 4.53 | −62.50 | −60.39 |
| 2b | 10 | 31.00 ± 4.2 | 11.00 ± 2.5 | −64.5 | −63.3 |
| 4 | 10 | 33.75 ± 2.76 | 17.00 ± 2.64 | −49.63 | −43.89 |
| Aminophyllin | 10 | 35.50 ± 11.50 | 14.50 ± 4.50 | −59.15 | −52.14 |

As it can be seen, the comparison with aminophyllin is indicative of a very remarkable activity of the various dioxolane derivatives which were tested. Said comparison becomes particularly favorable when the toxicity values, which incidentally are considerably advantageous by themselves, are taken into account, especially for the compounds of Examples 2, 2a and 2b.

For administration purposes, the compounds of the inventions can be embodied into suitable pharmaceutical dosage forms such as, for instance, tablets, capsules, sugar coated tablets and the like, in admixture with the commonly employed pharmaceutical excipients or carriers. They can also be compounded into suppositories, aerosols or into pharmaceutical formulations suitable for the intramuscular or intravenous administration.

What is claimed is:

1. Theophyllinylmethyldioxolane derivatives of the following general formula

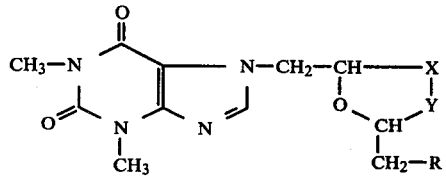

wherein:

X and Y are different from each other and represent —CH₂— or an oxygen atom; R represents a radical selected from hydroxy, bromo, acetoxy, pyrrolidino, morpholino, piperazino and piperazino substituted at the position 4 by a carbethoxy, benzyl, phenyl, halophenyl, methoxyphenyl or trifluoromethylphenyl group; or when X is —CH₂— and Y is an oxygen atom, R may also represent chloro.

2. Compounds as in claim 1, wherein X and Y are different from each other and represent —CH₂— or an oxygen atom, R represents a radical selected from bromo, acetoxy, pyrrolidino, morpholino and piperazino and, when X is —CH₂— and Y is an oxygen atom, R may also represent chloro.

3. A compound as in claim 1, which is 2-bromomethyl-4-(7'-theophyllinylmethyl)-dioxolane.

4. A compound as in claim 1 which is 4-pyrrolidinomethyl-2-(7'-theophyllinylmethyl)-dioxolane.

5. A compound as in claim 1 which is 4-morpholinomethyl-2-(7'-theophyllinylmethyl)-dioxolane.

6. A compound as in claim 1 which is 2-morpholinomethyl-4-(7'-theophyllinylmethyl)-dioxolane.

7. A compound as in claim 1 which is 2-acetoxymethyl-4-(7'-theophyllinylmethyl)-dioxolane.

8. A pharmaceutical composition useful for combatting cough diseases, which comprises an anticough effective amount of a compound as in claim 1 as the active ingredient in admixture with a suitable pharmaceutical excipient or carrier.

9. A pharmaceutical composition as in claim 8, wherein the active ingredient is 4-pyrrolidinomethyl-2-(7'-theophyllinylmethyl)-dioxolane.

10. A pharmaceutical composition as in claim 8, wherein the active ingredient is 4-morpholinomethyl-2-(7'-theophyllinylmethyl)-dioxolane.

11. A pharmaceutical composition as in claim 8, wherein the active ingredient is 2-morpholinomethyl-4-(7'-theophyllinylmethyl)-dioxolane.

12. A pharmaceutical composition as in claim 8, wherein the active ingredient is 2-acetoxymethyl-4-(7'-theophyllinylmethyl)-dioxolane.

* * * * *